United States Patent [19]

De Thomas et al.

[11] 4,083,809

[45] Apr. 11, 1978

[54] HYDROGENATION CATALYST AND METHOD OF PRODUCING SAME

[75] Inventors: Waldo De Thomas, Parsippany; Eugene V. Hort, Wayne, both of N.J.

[73] Assignee: GAF Corporation, New York, N.Y.

[21] Appl. No.: 716,111

[22] Filed: Aug. 20, 1976

[51] Int. Cl.$^2$ .................. B01J 21/06; B01J 23/42; B01J 23/44; B01J 23/72

[52] U.S. Cl. .................. 252/457; 252/460; 252/474; 260/343.6

[58] Field of Search ............ 252/460, 474, 457, 454; 260/343.6

[56] References Cited

U.S. PATENT DOCUMENTS

| 3,076,858 | 2/1963 | Frevel et al. | 252/474 X |
| 3,228,991 | 1/1966 | Dulaney et al. | 252/474 X |
| 3,274,286 | 9/1966 | Reich | 252/474 X |
| 4,001,282 | 1/1977 | Miller | 260/343.6 |
| 4,021,374 | 5/1977 | Petro et al. | 252/457 X |

Primary Examiner—W. J. Shine
Attorney, Agent, or Firm—Walter C. Kehm; Walter Katz

[57] ABSTRACT

Hydrogenation catalyst and a process for producing gamma-butyrolactone by hydrogenating a feed compound — selected from the group consisting of maleic acid, succinic acid, maleic anhydride, succinic anhydride, and mixtures of any of the foregoing — in the vapor phase, in the presence of said catalyst, which is a highly selective elemental Cu-Pd or Cu-Pt catalyst, in order to produce high yields of gamma-butyrolactone and minimize the formation of by-products.

3 Claims, No Drawings

HYDROGENATION CATALYST AND METHOD OF PRODUCING SAME

BACKGROUND OF THE INVENTION

1. Field of the Invention

The present invention relates to improved hydrogenation catalysts, a method of producing such catalysts, and to the production of gamma-butyrolactone with such catalysts from maleic acid, succinic acid, maleic acid, succinic acid, maleic anhydride, succinic anhydride, and mixtures thereof, and, more particularly, relates to highly selective hydrogenation catalysts comprising elemental Cu-Pd or Cu-Pt, a method of producing such catalysts, and an improved process for the production of gamma-butyrolactone by catalytically hydrogenating, in the vapor phase, a feed compound selected from the group consisting of maleic acid, succinic acid, maleic anhydride, succinic anhydride, and mixtures of any of the foregoing with or without butyrolactone, in the presence of said highly selective hydrogenation catalysts.

2. DESCRIPTION OF THE PRIOR ART

Gamma-butyrolactone is a stable, well known compound that is a liquid at $-44°$ C. to $204°$ C. It is preferably used as an intermediate, e.g., in the manufacture of 2-pyrrolidone, α-tetralone, glutaric acid, etc. It is also useful in the solvent welding of plastic films; as a swelling agent for cellulose acetate films; and as a non-corrosive solvent for polymers in general, acetylene, and water-immiscible alcohols.

In general, the catalytic hydrogenation of maleic anhydride and/or other related compounds to produce gamma-butyrolactone (hereinafter referred to as "butyrolactone") is an old and well established art for which a great many processes have been used, the most important of which historically have been effected in the liquid phase.

Exemplary of such liquid phase processes are U.S. Pat. Nos. 2,772,291-3, which generally relate to high pressure hydrogenation of maleic anhydride to form various mixtures of butyrolactone, tetrahydrofuran, and butanediol in the presence of such catalysts as those of nickel-chromium-molybdenum, Raney-type nickel or cobalt, and nickel or cobalt molybdates. Later patents utilizing liquid phase, catalytic hydrogenation of conventional feedstocks, such as maleic anhydride, to butyrolactone have substantially dealt with modifications of those types of catalyst. For example, U.S. Pat. No. 3,312,718, relating generally to substantially complete conversion of succinic anhydride to butyrolactone, employs a hydrogenation catalyst, preferably of nickel, along with a silicotungstic acid as promoter.

Additionally, U.S. Pat. No. 3,113,138 discloses processes utilizing palladium catalysts, in the liquid phase, together with certain solvents, to obtain butyrolactone from succinic anhydride, but processes such as these have been characterized by a short catalyst life and have been unable to provide adequate yields.

An alternative to the commercially-used, liquid phase catalytic hydrogenation of maleic anhydride, succinic anhydride, etc., feedstocks essentially consists of vapor phase hydrogenation, at low pressures, in the presence of a generally different class or type of catalyst, but there has been much less activity in this area in general, and processes using vapor phase catalytic hydrogenation have not heretofore found commercial favor. Exemplary of patents covering vapor phase catalytic hydrogenation of conventional feedstocks to butyrolactone include, for example, U.S. Pat. No. 3,065,243, wherein the conversion to butyrolactone is effected at low pressure in the presence of a copper chromite catalyst. Later work in this field has included various catalyst modifications utilizing, e.g., different combinations of copper, chromium, and zinc, whereby, in some instances, Cu-Zn has been used; in other instances, a combination of Cu-Cr has been used; and, finally, in another combination, that of Cu-Cr-Zn has been used. Exemplary of this later work is U.S. Pat. No. 3,580,930, which describes the use of Cu-Cr-Zn.

In addition, among other conventional hydrogenation catalysts, there may be mentioned catalysts containing such metals as rhenium and rhodium, but neither of these is presently used for hydrogenation reactions of the type described herein and neither would be as acceptable as the catalysts previously described above.

However, commercial practice in respect of the production of butyrolactone from conventional maleic anhydride, succinic anhydride, etc., feedstocks by catalytic hydrogenation has not been entirely successful, especially in terms of both high activity and high yield. The present invention has been developed to fill this void, and provides elemental Cu-Pd and Cu-Pt catalysts, which not only retain the selectivity shown by copper alone without additives, but also have an activity much greater than that afforded by copper alone.

SUMMARY OF THE INVENTION

The present invention, as previously noted, is directed to improved hydrogenation catalysts, a method of producing same, and to an improved process for obtaining butyrolactone by catalytically hydrogenating, in the vapor phase, a feed compound, preferably one selected from the group consisting of maleic acid, succinic acid, maleic anhydride, succinic anhydride, and mixtures of any of the foregoing, in the presence of the highly selective hydrogenation catalysts containing metals of both copper and palladium or both copper and platinum and having a specific composition as hereinafter defined.

DESCRIPTION OF THE PREFERRED EMBODIMENTS

The present catalyst composition is one that is characterized by displaying, in addition to a very long active life, an activity of a much higher order of magnitude than either copper alone or in various admixtures with chromium and/or zinc, the materials previously used to promote the activity of copper. Furthermore, the present elemental Cu-Pd-, and Cu-Pt-containing catalysts are also capable of retaining the high selectivity of copper without additives, a feature to be contrasted with the fact that use of other hydrogenating additives, such as nickel and cobalt, which display high activity as hydrogenation catalysts, in the present catalysts, results in a decrease in selectivity. Similarly, other highly active hydrogenation catalysts such as ruthenium and rhodium are likewise unsatisfactory.

While the present feedstocks may contain both a carbonyl group and a site of ethylenic unsaturation, and while hydrogenation ordinarily is known to add to both such moieties under different conditions, normally in two separate steps, nevertheless, in view of the outstandingly high degree of selectivity and activity of the present Cu-Pd-, and Cu-Pt-containing catalysts, hydrogenation of both the carbonyl group and the site of ethylenic unsaturation can essentially be conducted in a single stage.

Maleic acid has the same skeletal structure as succinic acid and is known to yield the latter on catalytic hydrogenation. Succinic acid, in turn, readily forms the corresponding anhydride, one carbonyl group of which can be reduced, under carefully controlled hydrogenation conditions to form butyrolactone. Thus, it can readily be seen that all of the present starting materials are individually convertible to butyrolactone by catalytic hydrogenation and that the formation of butyrolactone from any of such materials or mixtures thereof, is a function of the degree of hydrogenation each of such starting materials requires during catalytic hydrogenation, such function itself being readily within the manipulative skill of the operator, based upon use of particular combinations of feed rates, mole ratios of reactants, temperatures, reaction times, reactor sizes, etc., as desired. In any event, all of the present feedstocks, with the exception of succinic anhydride, are presumably converted to succinic anhydride, the immediate precursor of butyrolactone which, upon further catalytic hydrogenation, is converted to butyrolactone. When the feedstocks, however, are maleic or succinic acid, it is preferable that such feedstocks be first dehydrated at elevated temperatures to the corresponding anhydrides prior to their contact with the hydrogenation catalyst in the reaction zone.

In accordance with a preferred embodiment of this invention, a feed compound, such as one of maleic acid, succinic acid, maleic anhydride, succinic anhydride, or mixtures of any of the foregoing, either with or without butyrolactone, is reacted, in the vapor phase, with hydrogen at elevated temperatures in the presence of a Cu-Pd or Cu-Pt catalyst, preferably the former. In conducting this reaction, the temperature that is employed therein can vary between about 150° C. and 350° C., and preferably between 180° C. and 330° C. Hydrogen is supplied to the reaction zone in a stoichiometric excess, preferably in such a quantity that the molar ratio of hydrogen to the anhydride is in excess of 5:1 and as high as 200:1 or even higher. The reactants are passed to the catalytic zone in the vapor phase, the rate of vaporization being susceptible to careful control, such as through the use of a vaporizer, and the reaction is carried out at low pressures, which may range from atmospheric up to about 50 atmospheres. Preferably, however, the pressure is between one and about ten atmospheres.

It is preferred that the contact time between the reactants in the reaction zone in the presence of the instant catalyst be of short duration, e.g., be in the range of about 2 to 10 seconds, since, for longer contact times than this, there may result an increased formation of by-products, such as tetrahydrofuran, for example.

The catalyst employed in the process of this invention comprises one containing, in the form of free metals, about 3 to about 100% by weight, preferably about 4 to about 30% by weight of an admixture of copper with palladium or platinum, preferably reduced copper-palladium or reduced copper-platinum, in which the ratio by weight of copper to palladium or platinum is about or more than about 10:1 and about or less than about 500:1, preferably between about 20:1 and about 250:1. The catalyst may be in the form of pellets, spheres, extrudate, granules, or any form suitable for packing a catalyst bed, or it may result from deposition of reduced Cu-Pd or Cu-Pt on a suitable carrier in a manner well known to those skilled in the art. It is preferable, however, that the catalyst be reduced with hydrogen at a temperature below about 300° C. to minimize sintering prior to use in the process of this invention.

As previously indicated, the present hydrogenation catalysts are characterized by containing either an admixture of copper and palladium or an admixture of copper and platinum, the former admixture being preferred and the one of choice. While palladium and platinum are of roughly equivalent activity and utility in the present hydrogenation catalysts, this is only the case under certain circumstances and conditions, owing in part to the nature of the catalyst and its method of preparation. For example, while there are a number of various alternative processes available by which to prepare a Cu-Pd catalyst, all of which lead to a catalyst of acceptable quality in terms, e.g., of its utility herein with respect to activity, selectivity, etc., nevertheless, this circumstance is not true in the present invention in respect of the Cu-Pt catalyst, where it has been found that, in order to obtain results for the Cu-Pt catalyst that are equivalent to those both desired and obtainable from the Cu-Pd catalyst, the Cu-Pt catalyst must not be prepared by many of those procedures by which the corresponding Cu-Pd catalyst can be prepared but must be prepared by a specific preparative technique. For example, the instant Cu-Pt catalyst can be prepared with a utility equivalent to that of Cu-Pd by being precipitated from a solution comprising salts of platinum and copper (and, optionally, a carrier such as magnesium silicate, if desired), dried, calcined and then reduced to the elemental form.

However, Cu-Pt catalysts of equivalent activity to that of Cu-Pd, unlike those comprising Cu-Pd, are not obtained when the following conventional methods and procedures are employed to prepare such Cu-Pt catalysts:

(1) Dip impregnation — wherein a preformed catalyst support is dipped into a hot concentrated solution of copper and platinum salts, then dried, calcined, and reduced.

(2) Dip impregnation — wherein the preformed catalyst support is added to a diluted copper and platinum salt solution, and the unabsorbed salt solution is then filtered and then recycled, this procedure being repeated several times. The impregnated support is then dried, calcined, and reduced.

(3) Impregnation by vacuum stripping — wherein a mixture of a catalytic metal salt solution and a catalyst support therefor are first vacuum stripped to dryness, then calcined, and reduced.

(4) Physically blending — wherein solid salts of the catalytic metals are physically blended with a catalyst support, and then calcined and reduced.

A preferred procedure for the prior reduction of the Cu-Pd or Cu-Pt catalyst is as follows:

First of all, an admixture of copper oxide and palladium oxide or platinum oxide, wherein the ratio of copper to palladium or platinum is preferably between 20:1 and 250:1, is heated to about 140° C. under an inert atmosphere, e.g., that of nitrogen. Hydrogen is then slowly added to the system at a rate such as to avoid a build-up of temperatures above 300° C. within the catalyst bed. The gas flowing over the catalyst bed is gradually enriched with hydrogen as the temperature is slowly raised to 300° C. At this temperature, the gas may be pure hydrogen. The catalyst is then held at this temperature until no further formation of any water of reduction is observed, whereupon the catalyst may then be used in the present process for producing butyrolactone.

As noted, the present catalyst can be used in a number of different forms, the choice of which is dependent upon whether or not the process of the present invention is carried out in a fixed bed reactor, or with a fluidized bed reactor, since the present catalyst can be adapted to suit either of these purposes.

In addition, the present catalyst can also be supported by various carriers conventionally used in standard hydrogenation reactions. A representative, non-limiting list of such carriers, which is not intended by any means to be exhaustive, includes such materials as magnesium silicate, silica gel, kieselguhr, alumina, asbestos, pumice, and those crystalline aluminosilicate materials known in the art as molecular sieves. Better results and less side reactions are obtained, however, with the non-acidic carriers; hence, non-acidic carriers are the preferred carriers for purposes of this invention, especially those of high surface area. These non-acidic carriers include magnesium silicate, silica gel, and asbestos. When a carrier is used, the preferred range of copper-palladium, or copper-platinum content in the overall catalyst is about 5–40% by weight.

The process for producing butyrolactone that is contemplated herein comprises, as noted, catalytic hydrogenation of a suitable feed compound in the presence of a Cu-Pd or Cu-Pt catalyst. Any reasonably pure grade of any of the aforementioned feedstocks or mixtures thereof is operable, the only precaution being necessary being that of insuring that the feedstock in question does not contain any materials that would poison the present catalyst. It is well known, for example, that materials such as halogens and many of the compounds containing same, as well as many nitrogen-and sulfur-containing compounds, are harmful to the activity of hydrogenation catalysts. Such materials, therefore, are preferably avoided in carrying out the process of the present invention. As noted, the reactants are passed to the catalytic zone in the vapor phase whereupon the reaction is effected at low pressures, ranging from atmospheric and upwards to about 50 atmospheres, preferably between one and about ten atmospheres.

Owing to the high selectivity of the present Cu-Pd and Cu-Pt catalysts, throughout the range of reaction conditions noted above, the reaction proceeds essentially to almost complete conversion of feedstock to butyrolactone with only moderate amounts of by-products formed such as tetrahydrofuran and butanol, each of which is obtained generally in minor amounts totalling about 2 to about 10 mole-percent of feedstock charged.

The invention will be further illustrated (but is not limited) by the following examples in which the quantities of reactants recited are by weight unless otherwise indicated. The feed rate, where given in the examples, is in parts of the feedstock per hour per volume of catalyst bed. The temperature of the catalyst bed in each example is the highest temperature observed in the catalyst bed. In the examples, the over-all material balance was substantially quantitative. The term "conversion", wherever used in the examples, is defined as the percentage of starting material consumed in the reaction. The term "selectivity", wherever used in the examples, is defined as the percentage of butyrolactone produced as compared to the total amount of starting material consumed. The metal content of the catalyst described in the Examples, unless otherwise stated, is in terms of elemental metal.

EXAMPLE 1

Catalyst Preparation

Respective solutions of 0.5 g. (0.0022 moles) of palladium nitrate in 100 ml. of water and a solution of 0.33 g. (0.001 moles) of platinum ammonium chloride in 100 ml. of water were each mixed with a solution of 80 g. (0.33 moles) of cupric nitrate trihydrate in 200 ml. of water. In each of the resulting solutions was slurried 79 g. of magnesium silicate. A solution prepared from 70 g. (0.66 moles) sodium carbonate in 200 ml. water was slowly added to each solution to precipitate the respective catalyst precursors. Each of the resultant slurries was filtered and washed with 1 liter of water in small portions. After drying at 200° C. for two hours and calcining at 450° C. for 5 hours, 90 g. of Cu-Pd catalyst powder, and 88 g. of Cu-Pt catalyst powder was obtained, whose oxides contained, as free metals, 21% copper and 0.3% palladium and 21% copper and 0.2% platinum, respectively. The resulting calcined catalyst powders were tableted in ⅛ inch diameter pellets.

EXAMPLE 2

A stainless steel reactor tube with an internal diameter of 1 inch and a length of 12 inches was packed with 55 g. of the Cu-Pd catalyst of Example 1. The catalyst was reduced over a six hour period at 150°–250° C. using 25% hydrogen in nitrogen, introduced intermittently until there was little exotherm, whereupon the hydrogen concentration was increased to 100% and the temperature raised to 300° C. for 2 hours. A feed of 100% maleic anhydride was carried through the reactor by a hydrogen stream through a vaporizer at 130°–190° C. The rate of vaporization was controlled by varying the temperature of the vaporizer. Maintaining the reactor at 285°–290° C. and the feed rate at 8 ml. per hour, the conversation was 92% and the selectivity was 95%.

EXAMPLE 3

A catalyst containing 10% copper and 0.1% palladium was used in equipment similar to that described in Example 2. At 240°–245° C., with a feed rate of 6 ml. per hour, the conversion was 97% and the selectivity was 96%.

EXAMPLE 4

A catalyst containing 6% copper and 0.05% palladium was used in similar equipment as described in Example 2. At 255°–260° C., with a feed rate of 7 ml. per hour, the conversion was 100% and the selectivity was 95%.

EXAMPLE 5

A catalyst containing 20% copper and 0.47% palladium was used in similar equipment as described in Example 2. At 260°–265° C., with a feed rate of 12 ml. per hour, the conversion was 96% and the selectivity was 91%.

EXAMPLE 6

A catalyst was prepared by the procedure of Example 1, using 12% copper and 0.1% palladium on a carrier compound of kieselguhr rather than of magnesium silicate, and employed in the standard equipment described in Example 2. At 275° C., with a feed rate of 7 ml. per hour, the conversion was 96% and the selectivity was 93%.

EXAMPLE 7

A catalyst was prepared by the procedure of Example 1 using 21% copper and 0.3% palladium on silica gel as carrier, and employed in the standard equipment described in Example 2. At 255° C., with a feed rate of 8 ml. per hour, the conversion was 98% and the selectivity was 92%.

EXAMPLE 8

The catalyst was prepared as in Example 1, except for the fact that copper was used with 1% palladium and no support was utilized. Analysis of the catalyst pellets before reduction gave 79% copper and 1% palladium. This catalyst was used in the same equipment as described in Example 2 at 280° C., with a feed rate of 6 ml. per hour. The conversion was 91% and the selectivity was 93%.

EXAMPLE 9

This example was conducted in the same manner as described in Example 2, except for use of 50% maleic anhydride in butyrolactone as the feed. With the feed rate of 16 ml. per hour, the conversion was 92% and the selectivity was 92%.

EXAMPLE 10

This example was conducted in the same manner as described in Example 2, except for use of a mixture of 50% maleic anhydride and succinic anhydride as feed. With the feed rate at 8 ml. per hour, the conversion was 95% and the selectivity was 93%.

EXAMPLE 11

A catalyst containing 15% copper and 0.2% nickel was used in similar equipment to that described in Example 2. At 305°–310° C., with a feed rate of 8 ml. per hour, the conversion was 92% and the selectivity was 70%.

EXAMPLE 12

A catalyst containing 27% copper on magnesium silicate (with no other catalytic metal present) was used in similar equipment to that described in Example 2. At 290°–295° C., with a feed rate of 4 ml. per hour, the conversion was 83% and the selectivity was 98%.

EXAMPLE 13

A catalyst containing 0.2% palladium on magnesium silicate (with no other catalytic metal present) was used in equipment similar to that described in Example 2. At 250° C., with a feed rate of 7 ml. per hour, the conversion was 95% and the selectivity was 21%.

EXAMPLE 14

The Cu-Pt catalyst of Example 1, containing 21% copper and 0.2% platinum, was used in equipment similar to that described in Example 2. At 305° to 310° C., with a 14 ml./hr. feed rate of 50% maleic anhydride in butyrolactone, the conversion was 92% and the selectivity was 96%.

EXAMPLE 15

A catalyst containing 21% copper and 0.2% ruthenium was used in equipment similar to that described in Example 2. At 285° to 290° C., with an 11 ml./hr. feed rate of 50% maleic anhydride in butyrolactone, the conversion was 81% and the selectivity was 74%.

EXAMPLE 16

A catalyst containing 21% copper and 0.2% rhodium was used in equipment similar to that described in Example 2. At 290° C. and with an 8 ml./hr. feed rate of 50% maleic anhydride in butyrolactone, the conversion was 92% and the selectivity was 42%.

In the following Examples 17–20, the catalyst described was prepared in accordance with the procedure set forth in Example 1.

EXAMPLE 17

A catalyst containing 10% copper and 0.1% platinum was used in equipment similar to that described in Example 2. At 280°–285° C., with a 12 ml./hr. feed rate of 50% maleic anhydride in butyrolactone, the conversion was 94% and the selectivity 95%.

EXAMPLE 18

A catalyst containing 6% copper and 0.05% platinum was used in equipment similar to that described in Example 2. At 280°–285° C, with a 6 ml./hr. feed rate of 100% maleic anhydride, the conversion was 100% and the selectivity 95%.

EXAMPLE 19

A catalyst containing 12% copper and 0.1% platinum was used in equipment similar to that described in Example 2. At 290°–295° C, with a 6 ml./hr. feed rate of 100% maleic anhydride, the conversion was 94% and the selectivity 93%.

EXAMPLE 20

A catalyst containing 20% copper and 0.5% platinum was used in equipment similar to that described in Example 2. At 285°–290° C., with a 7 ml./hr. feed rate of 100% maleic anhydride, the conversion was 98% and the selectivity 91%.

EXAMPLE 21

Preparation (partially by vacuum stripping) and Use of a Cu-Pt Catalyst (Comparative Example)

The catalyst was prepared by dissolving 160 grams of cupric nitrate in 300 ml. of water and adding 158 g. of magnesium silicate to make a slurry. A solution prepared from 140 g. of sodium carbonate in 300 ml. of water was slowly added to precipitate the catalyst precursor. The slurry was filtered and washed with 1 liter of water in small portions. After drying at 200° C. for 2 hours and calcining at 450° C. for five hours, 180 g. of catalyst powder was obtained containing 21% copper as the oxide. The resulting calcined catalyst powder was tableted in ¼ inch diameter pellets. 100 g. of these catalyst pellets were charged to a 500 cc flask, and a solution of 0.4 g. of platinum ammonium chloride in 100 cc. of water was added. This mixture was stirred, then the water was vacuum stripped at 70° C. and 1 mm Hg vacuum to dryness. The dried catalyst pellets containing the absorbed platinum salt were calcined at 450° C. for 5 hours and then reduced as per Example 2. The catalyst containing 21% copper and 0.2% platinum was then used in equipment similar to that described in Example 2. At 285° C. to 290° C. with a feed rate of 5 ml./hr., the conversion was 98% and the selectivity 35%.

The above results would have shown even poorer selectivity if both the copper and platinum had been fully impregnated into the support by the vacuum stripping technique, or by the various other conventional dip impregnation, or physical blending, techniques previously described above. Thus, this comparative example illustrates that special preparative means and a specific method are necessary in order for the present Cu-Pt catalyst to be obtained of a catalytic quality equivalent to that of the present Cu-Pd catalyst.

We claim:

1. A hydrogenation catalyst for the selective conversion of a feed compound selected from the group consisting of maleic acid, succinic acid, maleic anhydride, and succinic anhydride to gamma-butyrolactone in the vapor phase by hydrogenation consisting essentially of:
   a. an intimate admixture consisting of essentially metallic copper with a small amount of elemental metallic palladium or platinum therewith, on a magnesium silicate non-acidic carrier, wherein:
   b. said metals comprise about 4–30% by weight of said admixture, and
   c. the weight ratio of copper to said palladium or platinum being about 10:1 to about 500:1.

2. A hydrogenation catalyst for the selective conversion of a feed compound selected from the group consisting of maleic acid, succinic acid, maleic anhydride, and succinic anhydride to gamma-butyrolactone in the vapor phase by hydrogenation consisting essentially of:
   a. an intimate admixture consisting of essentially metallic copper with a small amount of elemental metallic palladium or platinum therewith, on a non-acidic carrier selected from the group consisting of magnesium silicate, asbestos, kieselguhr, and silica gel, wherein:
   b. said metals comprise about 4–30% by weight of said admixture, and
   c. the weight ratio of copper to said palladium or platinum being about 10:1 to about 500:1, wherein said admixture is prepared from a solution of soluble copper and palladium or platinum salts on a carrier from which copper and palladium or platinum has been precipitated and then converted to elemental form.

3. A hydrogenation catalyst according to claim 2 wherein said conversion is effected by reduction by heating in hydrogen below 300° C after drying and calcining the precipitating salts on a carrier.

* * * * *